United States Patent [19]

Zimmermann

[11] Patent Number: 5,543,520
[45] Date of Patent: Aug. 6, 1996

[54] PYRIMIDINE DERIVATIVES

[75] Inventor: Jürg Zimmermann, Wallbach, Switzerland

[73] Assignee: Ciba-Geigy Corporation, Tarrytown, N.Y.

[21] Appl. No.: 306,333

[22] Filed: Sep. 15, 1994

[30]  Foreign Application Priority Data

Oct. 1, 1993 [CH] Switzerland ............................ 2966/93
Jul. 18, 1994 [CH] Switzerland ............................ 2278/94

[51] Int. Cl.$^6$ ...................... C07D 239/42; C07D 401/04; C07D 403/04; C07D 409/04
[52] U.S. Cl. ............................................................ 544/331
[58] Field of Search .............................. 544/331; 514/275

[56]  References Cited

FOREIGN PATENT DOCUMENTS 0164204 12/1985 European Pat. Off. .
0233461  8/1987 European Pat. Off. .
0564409 10/1993 European Pat. Off. .

*Primary Examiner*—John M. Ford
*Attorney, Agent, or Firm*—Marla J. Mathias; Karen G. Kaiser; Irving M. Fishman

[57]  ABSTRACT

There are disclosed N-(fluoroalkoxyphenyl)-2-pyrimidine-amine derivatives of formula I

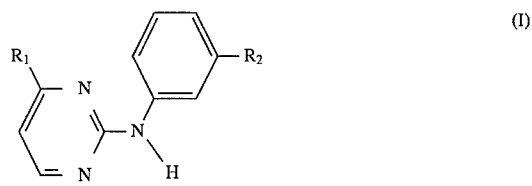

wherein $R_1$ is isoquinolinyl, thienyl or 1H-pyrrolyl, and $R_2$ is fluoro-substituted alkoxy containing up to 2 carbon atoms. These compounds can be used, inter alia, for the therapy of tumoral diseases.

7 Claims, No Drawings

PYRIMIDINE DERIVATIVES

The present invention relates to N-(fluoroalkoxyphenyl)-2-pyrimidine-amine derivatives, to their preparation, to medicaments containing said compounds, and to the use thereof for the preparation of pharmaceutical compositions for the therapeutic treatment of warm-blooded animals.

Specifically, the invention relates to N-(fluoroalkoxyphenyl)-2-pyrimidine-amine derivatives of formula I

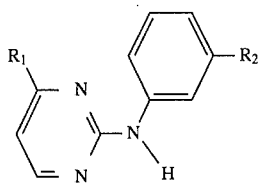

wherein $R_1$ is isoquinolinyl, thienyl or 1H-pyrrolyl, and $R_2$ is fluoro-substituted alkoxy containing up to 2 carbon atoms, and salts of such compounds containing a salt-forming group.

Isoquinolinyl is preferably 4-isoquinolinyl. Thienyl is preferably 2- or 3-thienyl. 1H-Pyrrolyl is preferably 1H-pyrrol-2-yl. Fluoro-substituted alkoxy containing up to 2 carbon atoms is typically trifluoromethoxy or, preferably, 1,1,2,2-tetrafluorothoxy.

Salt-forming groups in a compound of formula I are groups or radicals having basic properties. Compounds containing a basic radical, typically an isoquinolinyl radical, may form acid addition salts, typically with inorganic acids such as hydrochloric acid, sulfuric acid or a phosphoric acid, or with suitable organic carboxylic or sulfonic acids, conveniently aliphatic mono- or dicarboxylic acids such as trifluoroacetic acid, acetic acid, propionic acid, glycolic acid, succinic acid, maleic acid, fumaric acid, hydroxymaleic acid, malic acid, tartaric acid, citric acid, oxalic acid, or aminoacids such as arginine or lysine, aromatic carboxylic acids such as benzoic acid, 2-phenoxybenzoic acid, 2-acetoxybenzoic acid, salicylic acid, 4-aminosalicylic acid, aromatic-aliphatic carboxylic acids such as mandelic acid or cinnamic acid, heteroaromatic carboxylic acids such as nicotinic acid or isonicotinic acid, aliphatic sulfonic acids such as methanesulfonic acid, ethanesulfonic acid or 2-hydroxyethanesulfonic acid, or aromatic sulfonic acids, typically benzenesulfonic acid, p-toluenesulfonic acid or naphthalene-2-sulfonic acid.

Pharmaceutically unsuitable salts may also be used for isolating and purifying the compounds of formula I, and also for the compounds further used as intermediates. However, only the pharmaceuticayIly acceptable non-toxic salts are suitable for therapeutic use, for which reason they are preferred.

Because of the close relationship between the novel compounds in the free form and in the form of their salts, including also those salts that may be used as intermediates, for example for purifying or identifying the novel compounds, the references made throughout this specification with respect to the free compounds will be understood as referring also by analogy to the corresponding salts, whenever obtained.

The compounds of formula I have valuable pharmacological properties. Inter alia, they inhibit the protein kinase C enzyme with a high degree of selectivity. Protein kinase C, which is dependent on phospholipids and calcium, occurs within cells in a number of forms and participates in various fundamental processes such as signal transmission, proliferation and differentiation, as well as the release of hormones and neurotransmitters. This enzyme is activated either by receptor-mediated hydrolysis of phospholipids of the cell membrane or by direct interaction with specific tumour-promoting substances. The sensitivity of the cell to receptor-transmitted signal transmission can be substantially influenced by modulation of the enzymatic activity of protein kinase C (as signal transmitter). Compounds that are able to influence the activity of protein kinase C find utility as tumour-inhibiting, antiinflammatory, immunomodulating and antibacterial agents, and are even of interest as medicaments for treating athererosclosis and diseases of the cardiovascular system and central nervous system.

Formerly, protein kinase C from pig brain, which is purified by the method described by T. Uchida und C. R. Filburn in J. Biol. Chem. 259, 12311–4 (1984), was used to determine the inhibitory action on protein kinase C, and the inhibitory action on protein kinase C was determined by the method of D. Fabbro et al., Arch. Blochem. Biophys. 239, 102–111 (1985).

The protein kinase C from pig brain formerly used is a mixture of different subtypes (isotypes) of protein kinase C. If pure recombinant isotypes are used in the above assay instead of protein kinase C from pig brain, it is found that the compounds of formula I inhibit preferably the other "conventional" α-isotypes, whereas the other "conventional" β-1, β-2- and γ-isotypes, as well as in particular the "non-conventional" δ-, ε- and η-isotypes and the "atypical" ζ-isoform, are inhibited to a lesser degree or are virtually not inhibited at all.

Recombinant PKC isotypes are cloned, expressed and purified as follows:

The preparation of different proteins using baculoviruses and their cloning and isolation from Sf9 insect cells is carried out as described by M. D. Summers and G. E. Smith, "A manual method for baculovirus vectors and insect cell culture procedure", Texas Agricul. Exptl. Station Bull. (1987), 1555. The construction and isolation of recombinant viruses for the expression of PKC-α (beef), PKC-β1 (human), PKC-β2 (human) as well as PKC-γ (human/beef hybrid) in Sf9 cells is carded out as described by Stabel et al. [S. Stabel, M. Liyanage and D. Frith, "Expression of protein kinase C isozymes in insect cells and isolation of recombinant proteins", Meth. Neurosc. (1993)]. The preparation of the PKC isotypes in Sf9 cells is carried out as described by Stabel et al. (q. v. above), and the purification of the enzymes is carried out by the method described in the publication of McGlynn et al. [E. McGlynn, J. Liebetanz, S. Reutener, J. Wood, N. B. Lydon, H. Hofstetter, M. Vanek, T. Meyer and D. Fabbro, "Expression and partial characterization of rat protein kinase C-δ and protein kinase C-ζ in insect cells using recombinant baculovirus", J. Cell. Biochem. 49, 239–250 (1992)]. The generation of recombinant PKC-δ (rats), PKC-ε (rats), PKC-ζ (rats) ad PKC-η (mice), and their expression and purification, is carried out in accordance with the procedure described by Liyanage et. al. ["Protein kinase C group B members PKC-δ, -ε, ζ- and PKC-λ: Comparison of properties of recombinant proteins in vitro and in vivo", Biochem. J. 283,781–787 (1992)]and McGlynn et. al. (q. v. above), using additionally for the expression of PKC-η the transfer vector pAc360 [V. Luckow and M. D. Summers, "Trends in the development of baculovirus expression", Biotechnology 6, 47–55 (1988)].

The measurement of the activity of the recombinant PKC isotypes obtained by the above method is carried out in the absence of lipid and calcium (co-factors). This is done by using protamine sulfate, which is phosphorylated in the absence of co-factors, as substrate. The activity of the enzymes reflects the transfer of $^{32}P$ from $\gamma\text{-}[^{32}P]$-ATP to protamine sulfate. Protamine sulfate is a mixture of polypeptides, each containing four C-terminal arginine radicals. The measuremere of the phosphate incorporation is carried out under the following conditions: 100 μl of the reaction mixture contain in final concentrations 20 mM of TRIS-HCl pH 7.4, 10 mM of Mg[NO$_3$]$_2$, 0.5 mg/ml of protamine sulfate, 10 μM of ATP (0.1 μCi γ-[$^{32}$P]-ATP; 10 Ci/mol; Amersham, Little Chalfont, United Kingdom), different concentrations of the inhibitory substances and 0.5–2.5 U (units; one unit is the amount of enzyme which, in one minute per milligram of protein, transfers one nanomol $^{32}$P of the above mentioned γ-[$^{32}$P]-ATP to histone H1 [sigma, type V-S]) of the enzymes. The reaction is initiated by addition of the enzymes and transfer to 32° C. The reaction time is 20 minutes. Afterwards the reaction is halted by the dropwise addition of aliquots of 50 μl on to P81 chromatography paper (Whatman, Maidstone, United Kingdom). After removal of unbound γ-[$^{32}$P]-ATP and fraction nucleotides by washing procedures as described by J. J. Wilt and R. Roskoski, "Rapid protein kinase assay using phosphocellulose-paper absorption", Anal. Biochem. 66, 253–258 (1975), the substrate phosphorylation is determined by scintillation measurement. In this assay, the compounds of formula I inhibit the α-isotypes of protein kinase C (PKC) at an IC$_{50}$ concentration of about 0.1 to 5.0 μmol/liter, usually ot about 0.1 to 1.0 μmol/liter. The other isotypes of PKC are by comparison usually inhibited only at markedly higher (i.e. up to more than 300-fold) concentrations.

The compounds of formula I inhibit other enzymes, e.g. protein kinase A, only at a substantially higher concentration, e.g. 1000-fold, or not at all. This shows the selectivity of the compounds of formula I.

As may already be expected in the light of the inhibitory action on protein kinase C described above, the compounds of formula I have antiproliferative properties which can be demonstrated direct in the following other assay. In this assay, the inhibitory action of compounds of formula I on the growth of human T24 bladder carcinoma cells is determined. These cells are incubated in "Eagle's minimal essential medium", to which 5% (v/v) of foetal calf serum has been added, in a humidified incubator at 37° C. and 5 percent by volume of CO$_2$ in air. The carcinoma cells (1000–1500) are inoculated in 96-well microtitre plates and incubated overnight under the stated conditions. The test compound is added in serial dilutions on day 1. The plates are incubated for 5 days under the stated conditions. During this time the control cultures undergo at least 4 cell divisions. After incubation, the cells are fixed with a 3.3% (g/v) aqueous solution of glutaraldehyde, washed with water and stained with a 0.05% (weight/volume) aqueous solution of methylene blue. After washing, the stain is eluted with 3% (g/v) aqueous hydrochloric acid. Afterwards, the optical density (OD) per well, which is directly proportional to the number of cells, is measured with a photometer (Titertek multiskan) at 665 nm. The IC$_{50}$ values are computed by a computer system, using the formula $$\frac{OD_{665} \text{ (test) minus } OD_{665} \text{ (start)}}{OD_{665} \text{ (control) minus } OD_{665} \text{ (start)}} \times 100$$

The IC$_{50}$ values are defined as that active compound concentration at which the number of cells per well at the end of the incubation period is only 50% of the number of cells in the control cultures. The IC$_{50}$ values so obtained in this assay for the compounds of formula I are from about 0.1 to 9 μmol/liter.

The tumour-inhibiting activity of the compounds of formula I can also be demonstrated in vivo.

The tumour-inhibiting activity is determined using female Balb/c nude mice in which human T24 bladder carcinoma has been transplanted. On day 0, a c. 25 mg piece of solid tumour is transplanted subcutaneously under peroral "forene" narcosis on the left flank and the small incision wound is closed with a suture clip. On day 6 after the tumour transplantation, the mice are randomised in groups of 6 animals and treatment is commenced. The treatment is carried out for 15 days by administering a compound of formula I in dimethyl sulfoxide/Tween 80/sodium chloride solution in the different doses perorally or intraperitoneally once daily. The tumours are measured twice weekly with a sliding caliper and the tumour volume determined. In this assay, the peroral or intraperitoneal administration of a compound of formula I effects a marked reduction in the average tumour volume compared with the untreated controls.

Owing to the described properties, the compounds of formula I can be used in particular as tumour-inhibiting agents, inter alia for the treatment of tumours of the bladder and the skin. When the compounds of formula I are used in cancer therapy in conjunction with other chemotherapeutic agents, they prevent the development of resistance (multidrug resistance) or they neutralise an already existing resistance to the other chemotherapeutic agents. In addition, the compounds of formula I are suitable for the other utilities mentioned in connection with protein kinase C modulators, and they can be used in particular for the treatment of diseases that respond to inhibition of protein kinase C.

Some of the compounds of formula I furthermore inhibit the tyrosine kinase activity of the receptor for the epidermal growth factor (EGF). This receptor-specific enzyme activity is a key factor in the signal transmission in a host of mammalian cells, including human cells, especially epithelial cells, cells of the immune system and cells of the central and peripheral nervous system. The EGF-induced activation of the receptor-associated protein tyrosine kinase (EGF-R-PTK) is in many cells a prerequisite for cell division and hence for the proliferation of a cell population. The addition of EGF-receptor-specific tyrosine kinase inhibitors thus inhibits the replication of these cells.

The inhibition of the EGF-receptor-specific protein tyrosine kinase (EGF-R-PTK) can be demonstrated, inter alia, by the method of E. McGlynn et al., Europ. J. Biochem. 207, 265–275 (1992). The compounds of this invention inhibit enzyme activity by 50% (IC50) typically in a concentration of 0.1 to 10 μm.

These compounds of formula I, which inhibit the tyrosine kinase activity of the receptor for the epidermal growth factor (EGF) are therefor useful, inter alia, for the treatment of benign or malignant tumours. They are able to effect tumour regression and to prevent metastasic spread and the growth of micrometastases. In particular, they can be used for treating epidermal hyperproliferation (psoriasis), for treating neoplasms of epithelial character, e.g. mastocarcinomas, and leucemias. In addition, the compounds of formula I are useful for treating diseases of the immune system and inflammations, subject to the involvement of protein kinases. These compounds of formula I can also be used for treating diseases of the central or peripheral nervous system, subject to the involvement of signal transmission by protein kinases.

The compounds of formula I and the salts thereof also inhibit the enzyme p34$^{cdc2}$/cycline B$^{cdc13}$ kinase. That kinase controls, in addition to other cdc2-related kinases, specific phases of cell division, especially the transition from the G$_1$-phase to the S-phase and more especially the transition from the G$_2$phase to the M-phase.

In chronological order, the cycle of a eukaryotic cell consists of the interphase and the M-phase. The interphase is accompanied by an increase in the size of the cell. In chronological order, the interphase consists for its part of the $G_1$-phase, the S-phase and the $G_2$-phase. In the $G_1$-phase (G=gap) biosynthetic processes take place in the cell. In the S-phase (synthesis phase) the DNA doubles. The cell then enters the $G_2$-phase which ends with the commencement of mitosis.

In chronological order, the M-phase for its part consists of the division of the cell nucleus (mitosis) and the division of the cytoplasm (cytokinesis).

The above-mentioned inhibition of the enzyme $p34^{cdc}$/cycline $B^{cdc13}$ kinase can be demonstrated by the following test:

10 µM 1-methyl-adenine are used to induce starfish oocytes to enter the M-phase. The oocytes are then frozen in liquid nitrogen and stored at −80° C. If necessary, the oocytes are homogenised and centrifuged, as described in D. Arion et al., Cell 55, 371–378 (1988) and V. Rialet and L. Meijer, Anticancer Res. 11, 1581–1590 (1991). In order to purify the $p34^{cdc2}$/cycline $B^{cdc13}$ kinase, the supernatant of the oocytes is added to $p9^{CKShs}$-Sepharose grains prepared from recombinant human protein $p9^{CKShs}$, as described in L. Azzi et al., Eur. J. Biochem. 203, 353–360 (1992). After 30 minutes at 4° C. while being turned constantly, the grains are washed thoroughly and the active $p34^{cdc2}$/cycline $B^{cdc13}$kinase is eluted with free protein $p9^{CKShs}$ (3 mg/ml). The eluted kinase is tested using histone H1 as substrate, as described in L. Meijer et al., EMBO J. 8, 2275–2282 (1989) and EMBO J. 10, 1545–1554 (1991). In that test, the compounds of formula I and their salts exhibit an inhibiting concentration IC50 [µmol/liter] of approximately from 0.0005 to 2, in most cases approximately from 0.001 to 0.4.

That finding would also lead to the expectation that the compounds of formula I and the salts thereof can be used in the treatment of hyperproliferative disorders, such as tumours and psoriasis.

The compounds of formula I also inhibit the production of HIV viruses, as shown by the test below, and can accordingly be used as agents against the immune deficiency disease AIDS. The initial symptoms observed after HIV infection in humans is followed by a clinical latency period which can last several years. After that period, the stage known as AIDS occurs and usually progresses to death. The latency period is attributed to several factors: immune response, occlusion of the viruses in lymph nodes or other tissue and entry into a stage of molecular and viral latency in which the infected cells do not complete the viral cell cycle, which is why infectious viruses cannot be produced and the infection cannot spread. That stage of molecular latency has been investigated using cell models, such as the ACH-2 cell line [K. Clouse et at., J. Immunol. 142, 431 (1989)] and the U1 cell line [T. Folks et at., J. Immunol. 140, 117 (1988)]. Those cells are infected with HIV-1 viruses, but have only a low content of infectious viruses. If, however, those cells are stimulated with physiologically relevant factors that are known to be increased in AIDS patients, such as tumour necrosis factor, interleukin-6 etc., or with chemical inductors, such as phorbol diesters, for example 13-O-acetyl-12-O-n-tetradecanoyl-phorbol, a massive production of virus follows. The ACH-2 and U1 cells are representatives of two different cell families that are targets for HIV infection, namely lymphocytes and macrophages. Hitherto, effective prevention of the progression of HIV infection to the outbreak of AIDS has not been possible. Many attempts have been made to prevent virus replication after the outbreak of AIDS, that is to say, in a stage in which viruses are produced on a massive scale. In contrast, the compounds of formula I interfere with cell processes that lead to the activation of latently infected HIV cells without impairing normal cell processes, such as cell division.

If the above-mentioned U1 or ACH-2 cells are used as a model for viral latency, it can be demonstrated that HIV virus production induced by 13O-acetyl-12-O-n-tetradecanoylphorbol or tumour necrosis factor-alpha are effectively inhibited by the compounds of formula I at a concentration of approximately from 0.001 to 1 µmol/liter, for example at 0.03 µmol/liter.

A preferred group of compounds of formula I embraces those wherein $R_2$ is trifluoromethoxy or, preferably, 1,1,2,2-tetrafluoroethoxy, and salts of such compounds containing a salt-forming group.

A further preferred group of compounds of formula I embraces those wherein $R_1$ is 4-isoquinolinyl, 2- or 3-thienyl or 1H-pyrrol-2-yl, and $R_2$ is trifluoromethoxy or, preferably, 1,1,2,2-tetrafluoroethoxy, and salts of such compounds containing a salt-forming group.

The most preferred compounds of formula I are the compounds of formula I described in the Examples, first and foremost N-[3-(1,1,2,2-tetrafluoroethoxy)phenyl]-4-(4-isoquinolyl)-2-pyrimidine-amine and its salts.

The compounds of formula I and the salts of such compounds containing a salt-forming group are prepared by processes known per se. The process according to the present invention comprises reacting a compound of formula

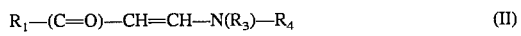

$$R_1—(C=O)—CH=CH—N(R_3)—R_4 \qquad (II)$$

wherein $R_3$ and $R_4$ are each independently of the other lower alkyl and $R_1$ is as defined above, or a salt or such a compound, with a compound of formula III

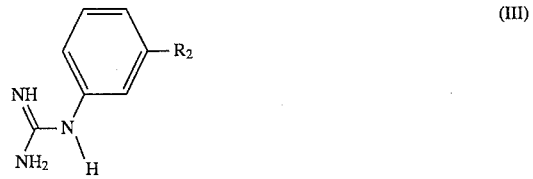

wherein $R_2$ has the meanings given above, or with a salt of such a compound, and, if desired, converting an obtained compound of formula I into a salt thereof, or converting a salt of a compound of formula I into the free compound.

The manner in which the above process variant is carried out is illustrated in more detail hereinafter.

$R_3$ and $R_4$ are preferably each methyl.

A salt of a compound of formula III is preferably an acid addition salt, typically a nitrate or one of the acid addition salts mentioned in connection with the final products of formula I.

The reaction is carried out in a suitable solvent or suspension agent, conveniently a suitable alcohol such as 2-methoxyethanol or a suitable lower alkanol such as isopropanol or isobutanol, in the temperature range from room temperature (c. 20° C.) to 150° C., conveniently under reflux. Especially if the compound of formula III is used as salt, said salt is converted into the free compound, preferably in situ, by addition of a suitable base, typically an alkali metal hydroxide, e.g. sodium hydroxide. The starting material of formula II is obtained by reacting a compound of formula IV

(IV)

wherein R₁ has the meanings given above, with a compound of formula V

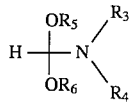

(V)

wherein $R_5$ and $R_6$ are each lower alkyl and the other substituents have the meanings given above, in general accordance with the procedure described in the European patent application published under number 233461. Typical examples of a compound of formula V are N,N-dimethylformamide dimethyl acetal and N,N-dimethylformamide diethyl acetal. The reaction may be carried out by heating the reactants of formulae IV and V for 1–24 hours in the absence or, if necessary, in the presence, of a solvent, to a temperature in the range from about 50° C. to 150° C.

Alternatively, the starting material of formula II is also obtained by reacting a compound of formula IV with ethyl formate of formula $H—C(=O)—O—CH_2—CH_3$ and reacting the resultant product with an amine of formula $H—N(R_3)—R_4$, wherein the substituents have the meanings given above.

The starting material of formula III is obtained in the form of an acid addition salt by reacting an aniline derivative of formula VI,

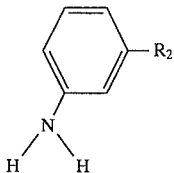

(VI)

wherein $R_2$ is as defined above, with cyanamide (NC—NH₂). The reaction is carried out in a suitable solvent or suspension agent, conveniently a suitable alcohol such as 2-methoxyethanol or a suitable lower alkanol such as ethanol, conveniently α) in the presence of equimolar amounts of the salt-forming acid, typically nitric acid, or β) in the presence of a substantial excess conveniently a 60% excess, of a mineral acid such as hydrochloric acid, and, upon termination of the reaction, adding an ammonium salt of the desired salt-forming acid, e.g. ammonium nitrate, in the temperature range from room temperature to 150° C., conveniently under reflux.

Acid addition salts of compounds of formula I are obtained in conventional manner, conveniently by treatment with an acid or a suitable anion exchange reactant.

Acid addition salts can be converted into the free compounds in conventional manner, typically by treatment with a suitable base.

Mixtures of isomers can be separated in per se known manner into the individual isomers, typically by fractional crystallisation, chromatography and the like.

The above described processes, are carried out in per se known manner, unless otherwise stated, typically in the absence or presence of preferably inert solvents or diluents, if necessary in the presence of condensing agents or catalysts, at reduced or elevated temperature, e.g. in the temperature range from about −20° C. to about +150° C., typically from about 0° C. to about +70° C., preferably from about +10° C. to about +50° C., mainly at room temperature, in a suitable reactor and if necessary, in an inert gas atmosphere, conveniently a nitrogen atmosphere.

Having regard to all substituents present in the molecule, the process will be carried out employing, if necessary, e.g. when readily hydrolysable radicals are present, mild reaction conditions such as short reaction times, the use of mild acids or bases in low concentration, stoichiometric proportions, choice of suitable catalysts, solvent, temperature and/or pressure conditions.

The invention also relates to those embodiments of the process in which a compound obtainable as intermediate in any stage of the process is used as starting material and the missing steps are carried out, or the process is discontinued in any stage or a starting material is formed under the reaction conditions or is used in the form of a reactive derivative or salt. It is preferred to use those starting materials which, in the practice of this invention, lead to the compounds described above as especially valuable.

The invention further relates to novel starting materials and/or intermediates as well as to processes for their preparation. The starting materials employed and the reaction conditions chosen are preferably those that lead to the compounds described in this specification as being especially preferred.

The invention also relates to a method of treating warm-blooded animals suffering from a tumoral disease, which comprises administering to warm-blooded animals in need of such treatment an effective, tumour-inhibiting amount of a compound of formula I or of a pharmaceutically acceptable salt thereof. The invention further relates to the use of a compound of formula I or of a pharmaceutically acceptable salt thereof for inhibiting protein kinase C in warm-blooded animals or for the preparation of pharmaceutical compositions for use in the therapeutic treatment of the human or animal body. It is contemplated that, depending on the species, age, individual condition, mode of administration and the particular clinical picture, daily doses of c. 1–1000 mg, preferably 50–500 mg, will be administered to a warm-blooded animal of 70 kg body weight.

The invention also relates to pharmaceutical compositions which contain an effective amount of the active compound, preferably an amount effective for the prevention or therapy of one of the aforementioned diseases, together with pharmaceutically acceptable carriers that are suitable for topical, enteral, for example oral or rectal, or parenteral administration, and which may be inorganic or organic, solid or liquid. For oral administration it is preferred to use tablets or gelatin capsules that contain the active compound together with a diluent such as lactose, dextrose, suchrose, mannitol, sorbitol, cellulose and/or glycerol, and/or glidants, typically diatomaceous earth, talcum, stearic acid or salts thereof such as magnesiun or calcium stearate, and/or polyethylene glycol. Tablets may also contain binders such as magnesium aluminium silicate, starches such as maize, corn or rice starch, gelatin, methyl cellulose, sodium carboxymethyl cellulose and/or polyvinyl pyrrolidone and, if desired, disintegrators such as starches, agar, alginic acid or a salt thereof, e.g. sodium alginate, and/or effervescent mixtures, or absorbents, colorants, flavourings and sweeteners. The pharmacologically active compounds of this invention can also be used in the form of compositions for parenteral administration or of infusion solutions. Such solutions are preferably isotonic aqueous solutions or suspensions which, in the case of lyophilised compositions that contain the active compound by itself or together with a carrier such as mannitol, can be prepared before use. The pharmaceutical compositions can be sterilised and/or can contain adjuvants such as preservatives, stabilisers, wetting agents and/or emulsifiers, solubilisers, salts for regulating the osmotic pressure and or buffers. The novel pharmaceutical compositions which, if desired, may contain further pharmacologically active substances such as antibiotics, are prepared in per se known manner by conventional mixing, granulating, sugar-coating, solution or lyophilising methods and contain from about 1% to 100%, preferably from about 1% to about 20%, of active compound.

The invention is illustrated by the following non-limitative Examples. The $R_f$ values are determined on silica gel thin-layer plates (ex Merck, Darmstadt, Germany). The ratio of the eluants to each other in the eluant mixtures is given in parts by volume (v/v), and temperatures are given in degrees Celsius.
Abbreviations:
HV: high vacuum
n: normal (straight-chain)
rotovap: rotary evaporator
RT: room temperature

EXAMPLE 1

To a solution of 100 mg (0.61 mmol) of 3-dimethylamino-(1H-pyrrol-2-yl)2-propen-1-one [described in EP-A-0 233 461]in 4 ml of isobutanol are added 185 mg (0.60 mmol) of 3-(1,1,2,2-tetrafluoroethoxy)phenylguanidine nitrate. Following the addition of 32.5 mg (0.81 mmol) of sodium hydroxide, the reaction mixture is stirred for 3 hours at 110° C. The suspension is concentrated under reduced pressure, the residue is dissolved in 4 ml of methylene chloride/tetrahydrofuran (1:1 ), and the solution is extracted with 2.4 ml of water. The organic phase is dried over sodium sulfate and concentrated on a rotovap. Recrystallisation from diethyl ether/tetrahydrofuran gives N-[3-(1,1,2,2-tetrafluoroethoxy)phenyl]-(1H-pyrrol-2-yl)-2-pyrimidine-amine; FAB-MS:353 (M$^+$+1 ), m.p. 142–143, $R_f$=0.83 (methylene chloride:methanol=9:1).

The starting material is obtained as follows:
Step 1.1
To a suspension of 25.2 g (120 mmol) of 3-(1,1,2,2-tetrafluoroethoxy)aniline in 125 ml of ethanol are added 10.1 g (240 mmol) of cyanamide (50% in water). Then 16.3 ml (192 mmol) of concentrated hydrochloric acid are added to the brown solution and the mixture is refluxed for 19 hours. After cooling to room temperature, the reaction mixture is concentrated under reduced pressure and the residue is dissolved in 80 ml of water. After addition of 19.2 g (240 mmol) of ammonium nitrate, the product is isolated. by filtration, washed with water and dried at 60° C. under HV, giving 3-(1,1,2,2-tetrafluoroethoxy)phenylguanidine nitrate; m.p. 132°–134° C.

EXAMPLE 2

In accordance with the eneral procedure described in Example 1, reaction of 100 mg (0.55 mmol) of 3-dimethylamino-1-(2-thienyl)-2-propen-1-one [described in EP-A-0 233 461] and 173 mg (0.55 mmol) of 3-(1,1,2,2-tetrafluoroethoxy)phenylguanidine nitrate gives N-[3-(1,1,2,2-tetrafluoroethoxy)phenyl]-4-(2-thienyl)-2-pyrimidine-amine; FAB-MS:370 (M$^+$+1), m.p. 115°–116°, $R_f$=0.95 (ethyl acetate).

EXAMPLE 3

In accordance with the general procedure described in Example 1, reaction of 10 g (0.055 mol) of 3-dimethylamino-(3-thienyl)-2-propen-1-one [described in EP-A-0 233 461] and 15 g (0.060 mol) of 3-(1,1,2,2-tetrafluoroet-hoxy)phenylguanidine nitrate gives N-[3-(1,1,2,2-tetrafluoroethoxy)phenyl]-4-(3-thienyl)-2-pyrimidine-amine; FAB-MS:370 (M$^+$+1), m.p. 110°–111°, $R_f$=0.8 (ethyl acetate:hexane=1:1).

EXAMPLE 4

In accordance with the general procedure described in Example 1, reaction of 226.2 mg (1.0 mmol) of 3-dimethylamino-(4-isoquinolyl)-2-propen-1-one and 185 g (0.60 mmol) of 3-(1,1,2,2-tetrafluoroethoxy)phenylguanidine nitrate gives N-[3-(1,1,2,2-tetrafluoroethoxy)phenyl]-4-(4-isoquinolyl)-2-pyrimidine-amine; FAB-MS:415 (M$^+$+1), m.p. 158°–160° C.

The starting material is obtained as follows:
Step 4.1
2.0 g (11.6 mmol) of 4-acetylisoquinoline [J. Chem. Soc., Perkin Trans. 1, (7), 1503–8]are stirred in 50 ml of dimethyl formamide diethyl acetal for 1 hour at 110° C. The reaction mixture is concentrated under reduced pressure and the residue is chromatographed (methylene chloride:methanol=95:5), giving 3-dimethylamino-1-(4-isoquinolinyl)-2-propen-1-one; $^1$H-NMR (dimethyl sulfoxide): 2.9 (3H,s), 3.1 (3H,s), 5.52 (1H,d), 7.7–8.2 (m,5H), 8.6 (1H,s), 9.35 (1H,s).

EXAMPLE 5

Tablets comprising 20 mg of active ingredient, e.g. one of the compounds of formula I described in Examples 1–4 and having the following composition, are prepared in conventional manner:
Composition:

| | |
|---|---|
| active ingredient | 20 mg |
| wheat starch | 60 mg |
| lactose | 50 mg |
| colloidal silicic acid | 5 mg |
| talcum | 9 mg |
| magnesium stearate | 1 mg |
| | 145 mg |

Preparation:
The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plasticised mass is obtained.

The plasticised mass is passed through a sieve of c. 3 mm mesh size and dried, and the resulting dry granulate is again passed through a sieve. Then the remainder of the wheat starch, the talc and the magnesium stearate are blended in and the mixture is compressed to 145 mg tablets with a breaking notch.

EXAMPLE 6

Capsules comprising 10 mg of active ingredient, e.g. one of the compounds of formula I described in Examples 1–4 are prepared in conventional manner as follows:
Composition:

| | |
|---|---|
| active ingredient | 2500 mg |
| talcum | 200 mg |
| colloidal silicic acid | 50 mg |

Preparation:

The active ingredient is intimately mixed with the talcum and the colloidal silicic acid and the mixture is forced through a sieve of 0.5 mm mesh size and then filled in 11 mg portions into hard gelatin capsules of suitable size.

What is claimed is:

1. A N-(fluoroalkoxyphenyl)-2-pyrimidine-amine derivative of formula I

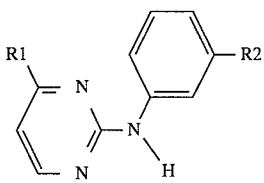

(I)

wherein $R_1$ is isoquinolinyl or 1H-pyrrolyl, it being possible for each of these two radicals to be bonded to the pyrimidine moiety via any one of its ring atoms, or $R_1$ is 2-thienyl or 3-thienyl, and $R_2$ is fluoro-substituted alkoxy containing up to 2 carbon atoms, or a salt of such a compound containing a salt-forming group.

2. A compound of formula I according to claim 1, wherein $R_2$ is trifluoromethoxy or 1,1,2,2-tetrafluoroethoxy, or a salt of such a compound containing a salt-forming group.

3. A compound of formula I according to claim 1, wherein $R_1$ is 4-isoquinolinyl, 2- or 3-thienyl or 1H-pyrrol-2-yl, and $R_2$ is trifluoromethoxy or 1,1,2,2-tetrafluoroethoxy, or a salt of such a compound containing a salt-forming group.

4. A compound of formula I according to claim 1, wherein $R_2$ is 1,1,2,2-tetrafluoroethoxy, or a pharmaceutically acceptable salt thereof containing a salt-forming group.

5. A compound of formula I according to claim 3, wherein $R_2$ is 1,1,2,2-tetrafluoroethoxy, or a pharmaceutically acceptable salt thereof containing a salt-forming group.

6. N-[3-(1,1,2,2-tetrafluoroethoxy)phenyl]-4-(4-isoquinolyl)-2-pyrimidine-amine or a pharmaceutically acceptable salt thereof as claimed in claim 1.

7. A compound of formula I according to claim 1 selected from N-[3-(1,1,2,2-tetrafluoroethoxy)phenyl]-(1H-pyrrol-2-yl)-2-pyrimidine-amine, N-[3-(1,1,2,2-tetrafluoroethoxy)phenyl]-4-(2-thienyl)-2-pyrimidine-amine, N-[3-(1,1,2,2-tetrafluoroethoxy)phenyl]-4-(3-thienyl)-2-pyrimidine-amine.

* * * * *